(12) United States Patent
Serteyn et al.

(10) Patent No.: US 8,399,208 B2
(45) Date of Patent: *Mar. 19, 2013

(54) METHOD AND KIT FOR THE MEASUREMENT OF NEUTROPHIL CELL ACTIVATION

(75) Inventors: Didier Serteyn, Tavier (BE); Ginette Dupont, Liege (BE); Thierry Franck, Remicourt (BE); Stéphane Kohnen, Malmedy (BE)

(73) Assignee: Universite de Liege, Leige (BE)

( * ) Notice: Subject to any disclaimer, the term of this patent is extended or adjusted under 35 U.S.C. 154(b) by 675 days.

This patent is subject to a terminal disclaimer.

(21) Appl. No.: 10/597,636

(22) PCT Filed: Feb. 7, 2005

(86) PCT No.: PCT/BE2005/000017
§ 371 (c)(1),
(2), (4) Date: Jun. 2, 2008

(87) PCT Pub. No.: WO2005/075986
PCT Pub. Date: Aug. 18, 2005

(65) Prior Publication Data
US 2008/0233600 A1    Sep. 25, 2008

(30) Foreign Application Priority Data
Feb. 6, 2004  (EP) .................................. 04447027

(51) Int. Cl.
*G01N 33/00* (2006.01)
*G01N 33/53* (2006.01)
(52) U.S. Cl. ........ 435/7.24; 435/7.1; 435/7.2; 435/7.72; 435/7.92; 436/519; 436/524; 436/528; 436/538; 436/164; 436/172; 436/175; 422/430
(58) Field of Classification Search .................. 435/7.1, 435/7.2, 7.24, 7.72, 7.92; 436/524, 528, 436/538, 164, 172, 175, 519
See application file for complete search history.

(56) References Cited

U.S. PATENT DOCUMENTS
5,290,679 A * 3/1994 Terao et al. .................. 435/7.4
(Continued)

FOREIGN PATENT DOCUMENTS
WO        9961907 A1    12/1999
WO    WO 99/61907     * 12/1999
(Continued)

OTHER PUBLICATIONS

Deby-Dupont et al., Equine Neutrophil Myeloperoxidase in Plasma: design of a radio-immunoassay and first results in septic pathologies, Veterinary Immunology and Immunopathology 66: 257-271 (1998).*
Janckila et al. Tartrate-resistant Acid Phosphatase Isoform 5b as Serum Marker of Osteoplastic Activity, Clinical Chemistry 47 (1): 74-80 (2001).*
Patricia C. Andrews et al., "Quantitative Determination of Myeloperoxidase Using Tetramethylbenzidine as Substrate." Analytical Biochemistry, vol. 127, (1982), pp. 346-350.
(Continued)

*Primary Examiner* — Gail R Gabel
(74) *Attorney, Agent, or Firm* — Fitch, Even, Tabin & Flannery LLP

(57) ABSTRACT

The present invention is related to accurate detection methods for the measurement only of myeloperoxidase (MPO) levels or neutrophils, preferably equine neutrophils, in complex biological samples. The present invention is further related to ELISA and SIEFED assays for such detection. SIEFED detection sensitivity of active peroxidase activity was found to be enhanced by the addition of nitrite. Such MPO measurement finds its use in many applications such as the prediction, diagnosis and/or monitoring of pathologies correlated with neutrophil activation and/or destruction; the evaluation of drugs and/or immunomodulators; the assessment of immune responses, either natural and/or after treatment with immunomodulators and/or drugs; and the study of cells and their ability to fight microorganisms and/or to destroy them.

14 Claims, 10 Drawing Sheets

U.S. PATENT DOCUMENTS

| | | | | |
|---|---|---|---|---|
| 5,460,961 | A | * | 10/1995 | Deby et al. .................... 435/192 |
| 5,552,292 | A | * | 9/1996 | Uchida et al. ................ 435/7.23 |
| 5,698,518 | A | * | 12/1997 | Carson et al. .................. 514/9.7 |
| 2006/0257879 | A1 | * | 11/2006 | Wilson et al. ..................... 435/6 |
| 2010/0196926 | A1 | * | 8/2010 | Serteyn et al. ................. 435/7.4 |

FOREIGN PATENT DOCUMENTS

WO             0250550 A2     6/2002

OTHER PUBLICATIONS

OxisResearch, A Division of OXIS Health Products, Inc., Bioxytech MPO-EIA, Portland, Oregon, Mar. 2005, 8 pages.

Benbarek, H., et al., "Cytotoxicity of Stimulated Equine Neutrophils on Equine Endothelial Cells in Culture", Equine Veterinary Journal, vol. 32, No. 4, Jul. 2000, pp. 327-333.

Gerard M.P., et al., "The Characteristics of Intestinal Injury Peripheral to Strangulating Obstruction Lesions in the Equine Small Intestine", Equine Veterinary Journal, vol. 31, No. 4, Jul. 1999, pp. 331-335.

Grulke S., et al., "Plasma Myeloperoxidase Level and Polymorphonuclear Leukocyte Activiation in Horses Suffering from Large Intestinal Obstruction Requiring Surgery: Preliminary Results", Canadian Journal of Veterinary Research, vol. 63, No. 2, Apr. 1999, pp. 142-147.

McConnico Rebecca S., et al. "Myeloperoxidase Activity of the Large Intestine in an Equine Model of Acute Colitis", American Journal of Veterinary Research, vol. 60, No. 7, Jul. 1999, pp. 807-813.

Moore, Rustin M., et al., "Neutrophil Accumulation in the Large Colon of Horses During Low-Flow Ischemica and Reperfusion", American Journal of Veterinary Research, vol. 55, No. 10, Oct. 1994, pp. 1454-1463.

Mathy-Hartert Marianne et al., Purification of Myeloperoxidase from Equine Polymorphonuclear Leucocytes, Canadian Journal of Veterinary Research, vol. 62, No. 2, Apr. 1998, pp. 127-132.

Deby-Dupont G., et al., "Equine Neutrophil Myeloperoxidase in Plasma: Design of a Radio-Immunoassay and First Results in a Septic Pathologies", Veterinary Immunology and Immunopathology, vol. 66, No. 3-4, Dec. 1994, pp. 257-271.

* cited by examiner

| MPO (ng/ml) | Mean | SD (n=3) | CV (%) |
|---|---|---|---|
| 18,00 | 24,825 | 0,4850 | 1,95 |
| 12,00 | 10,585 | 0,2801 | 2,66 |
| 8,00 | 4,428 | 0,4323 | 9,76 |
| 5,30 | 1,250 | 0,0683 | 5,46 |
| 3,55 | 0,392 | 0,0213 | 5,43 |
| 2,37 | 0,144 | 0,0026 | 1,78 |
| 1,58 | 0,095 | 0,0041 | 4,34 |
| 1,05 | 0,060 | 0,0030 | 4,89 |

METHOD AND KIT FOR THE MEASUREMENT OF NEUTROPHIL CELL ACTIVATION

FIELD OF THE INVENTION

The present invention is related to methods and kits (or devices) for the measurement of equine myeloperoxidase (MPO), a specific enzyme of equine neutrophils, either in total [first method], or specifically in its active form [second method]. Said methods and kits (or devices), used independently or in combination, find improved applications in the veterinary field and can be adapted for application in human health care. The concept of the second method is applicable to any other enzyme.

BACKGROUND OF THE INVENTION

Myeloperoxidase (MPO) is a specific enzyme of polymorphonuclear leucocytes (also known as neutrophils), which are white blood cells specialized in the fight against micro-organisms by phagocytosis.

Pathogens are destroyed inside the neutrophils by proteinases and myeloperoxidase, this latter enzyme being specifically responsible for the production of a potent oxidant agent, hypochlorous acid (HOCl). This HOCl (bleach) allows the destruction of the bacterial polysaccharidic capsules that withstand proteinases. MPO thus plays a key role in the host defense against infection.

During their fight against micro-organisms, dying neutrophils release myeloperoxidase in the surrounding liquids and tissues. When the activation of the neutrophils is excessive and becomes uncontrolled (as in acute inflammation pathologies), the release of myeloperoxidase is important and high concentrations of this enzyme are reached in biological media or samples (plasma, tissues, ascite fluids, broncho-alveolar fluids, pleural fluid, lymph, urine, saliva, uterine irrigation liquids . . . ), leading to an increased risk of cytotoxicity (by myeloperoxidase capture into cells or binding on cell surface, with in situ production of oxidants).

Until now, in equine medicine, myeloperoxidase was measured by the detection of a peroxidase activity. However, said detection according to hitherto developed techniques is not specific for equine myeloperoxidase (a general peroxidase activity is detected), is tedious and not applicable to complex biological media and samples (such as plasma) due to the presence of proteins (albumin, lipoproteins, . . . ) and reducing agents that interfere with the enzymatic measurement.

No efficient technique has been developed hitherto for the measurement of the total concentration of equine myeloperoxidase in complex biological fluids (both cellular and acellular) and in tissues.

The presence of myeloperoxidase in alveoli and tissues is presently estimated by the measurement of a non-specific peroxidase activity after extraction.

There is an ever increasing demand for easy and improved diagnostic tests to measure MPO activity and concentrations, especially in horses. The design of a rapid and sound assay for equine myeloperoxidase measurement is highly wanted for the diagnosis of equine diseases and/or pathologies (such as for instance colics with a high mortality in Equidae, sepsis, acute lung injury, acute inflammation, . . . ). The choice between a clinical treatment, a surgical intervention (costly for the veterinary surgeon and for the breeder) or, at the worst, euthanasia of the animal will be easier to make and the decision taken will be better funded when good, rapid and reliable assays exist to diagnose excessive neutrophil activation and/or invasion.

Myeloperoxidase is known to be a specific marker for excessive neutrophil activation and/or invasion, in humans as well as other mammals such as horses. In horses, intestinal tissue scores correlated for instance positively with tissue MPO activity in adjacent specimens (Mc Connino et al., 1999, Am J Vet Res 60: 807-813). It has been established that the physiological values of plasma myeloperoxidase in healthy horses are significantly exceeded in several acute abdominal pathologies, in horses with large intestine strangulation and in horses which will not survive (Deby-Dupont et al, 1998, Vet Immunol Immunopathol. 66: 257-271; Grülke et al., 1999, Can J Vet Res. 63:142-7; Grülke, 2002, doctoral thesis, ISBN 2-930212-57-8). In humans, the plasma concentration of myeloperoxidase is currently taken as marker of neutrophil activation such as in cardiovascular diseases (Zhang et al., 2001, JAMA 286: 3126-2142).

STATE OF THE ART

The publication of Deby-Dupont et al. (1998, Vet Immunol Immunopathol. 66: 257-271) describes the preparation of a radioimmunological assay (RIA) which requires the use of radioactively labelled molecules, specialized equipment and specific authorization for the use of said radioactive isotope labels.

Said radioimmunological assay (RIA) is suitable for equine myeloperoxidase detection in total (without distinction between the active or non active forms of the enzyme, recognizing for instance also hemi-enzymes and the heavy subunits of MPO). The available RIA method is, however, not suitable for the targeted detection of enzymatically active myeloperoxidase. The RIA method can be used for myeloperoxidase detection in plasma, but is not suited for adequate and reliable detection of MPO in tissue samples and in complex biological media or samples (such as seminal plasma, broncho-alveolar lavage fluids, sputum, purulent liquids, abscess, pleural fluids, urine, saliva, uterine irrigation liquids, . . . ). An adequate and reliable measurement of MPO in complex media and samples is not possible, due to interferences of the medium leading to a proteolytic alteration of the labelled reference molecule ($^{125}$I-labelled myeloperoxidase), and due to the high viscosity, excessive lipid and low protein contents of the medium altering the double antibody complex formation and precipitation ("matrix effects").

The international patent application WO 99/61907 describes a method for measuring the activation status of leucocyte cells, which cannot distinguish between lymphocytes (T-lymphocytes, NK or B-lymphocytes), eosinophils, neutrophils, basophils, monocytes and macrophages. Said method further requires the presence of said cells (in casu the leucocyte cells) in the biological sample to be analyzed. The activation status of said leucocyte sub-population is obtained by the measurement of the size of the leucocytes and/or by the measurement of the peroxidase activity of said leucocyte cells. Among the total peroxidase activities detected are, at least, the peroxidase activities of eosinophils (due to eosinophil peroxidase: EPO) and of neutrophils (due to the myeloperoxidase: MPO).

The method described in WO 99/61907 thus detects all kinds of peroxidase activity, is not limited to myeloperoxidase activity per se, and measures peroxidase activity in general in neutrophils, eosinophils and other blood cell types. The method is merely confined to the measurement of peroxidase activity in a sample of isolated cells, wherein peroxidase activity is anyhow high due to the in situ release of enzymes by the cells.

Only active intracellular enzyme activity is measured in the method according to WO 99/61907, for instance via a flow cytometer or an automated haematology analyzer, which require the availability of highly skilled personnel.

The method of WO 99/61907 does not apply specifically to the measurement of myeloperoxidase from neutrophils and does not apply to complex acellular media such as plasma and to tissues. Therefore, this method is not specific enough for myeloperoxidase and will not allow the practitioner to identify clearly the presence/absence of a given disease, or the condition of a specific disease, which is characterized by a specific activation status of neutrophil cells.

Finally, depending on the oxydo-reduction status of the sample milieu, major artefacts could arise and affect the precision of detection when the person skilled in the art will apply the method described in the document WO 99/61907.

The document WO 02/50550 describes the use of recombinant human myeloperoxidase for obtaining oxidized lipoprotein and discloses corresponding monoclonal antibodies directed against them. Said antibodies are suitable for diagnostic, preventive and therapeutic uses, especially for diagnosing and determining cardiovascular risks linked to the presence of oxidized low density lipoproteins.

AIMS OF THE PRESENT INVENTION

The present invention aims to provide new methods and kits (or devices) for a specific measurement of neutrophil cell activation in a biological sample obtained from a mammal, preferably a horse.

A main aim of the present invention is to provide such methods and kits (or devices) which are specific for the measurement of myeloperoxidase obtained from mammalian, preferably equine neutrophils, in complex cellular or acellular biological media.

A further aim of the present invention is to provide methods and kits (or devices) which can characterize total (active and non-active) myeloperoxidase [first method], and to provide methods and kits (or devices) which can characterize exclusively active myeloperoxidase obtained from said neutrophil cells [second method]. Another aim of the invention is to provide methods and kits (or devices) to study the effects of ligands (drugs) of myeloperoxidase or to screen new compounds that interact with myeloperoxidase.

A last aim of the present invention is to provide improved methods and kits (or devices) for veterinary and medical applications.

SUMMARY OF THE INVENTION

The present invention is related to a method (preferably an in vitro method) to measure the activation status (activation and degranulation) of neutrophil cells present in a biological sample obtained from a mammal, preferably a horse, which method specifically measures the myeloperoxidase (MPO) content (only), said content being correlated with said neutrophil activation status, said method comprising the steps of:
    obtaining a biological sample, preferably a biological fluid from said mammal, said sample preferably containing said cells or containing MPO released by said cells,
    (immuno)capturing MPO that is present in said biological sample by specific antibodies,
    detecting and/or measuring either total (active and inactive) MPO or exclusively active MPO present in said biological sample,
    possibly comparing the measured MPO values with normal MPO (i.e. standard of reference or preestablished standard MPO levels used at reference) levels obtained from a significant number (more than 10, preferably more than 50, more preferably more than 200 or 1000 individuals) of "healthy" mammals (i.e. mammals that present mammal MPO levels and do not suffer from the following described diseases or symptoms) or optionally quantifying MPO levels using a standard MPO curve, and
    relating the MPO levels measured to an activity status of said neutrophils indicative of the presence, absence or condition of a disease or immunological status of the mammal patient;
said detection and/or measurements specifically and accurately representing total MPO levels or active MPO levels in any type of biological sample.

To measure the total MPO content, a method further referred to as a MYELO-ELISA was developed. To measure active MPO enzyme levels, a method further referred to as a MYELO-SIEFED was developed.

In a preferred embodiment said mammal is a horse and said myeloperoxidase (MPO) an equine myeloperoxidase.

Preferably, MPO standard curves and specific dilutions are established for the specific detection method used and, if possible, for the type of sample analyzed.

Advantageously, measured MPO values are "normalized" in view of mean MPO levels obtained from a significant number of healthy individuals or mammals, preferably horses. This can be of particular importance as it was observed that the response of neutrophils can be highly variable from one individual to another but also from one day to another for one and the same individual.

Advantageously, normalized MPO levels can be linked monitored to the absence or presence of a disease and/or pathology or can be linked to a specific condition or status therein, by comparing measured levels with cut-off values derived from measurements performed on a significant number of individuals with said disease and/or pathology and/or in a specific condition and/or status. As such, the methods according to the present invention can also be used to make predictions on the susceptibility of individuals and/or groups for certain diseases and/or pathologies. Such prediction could be highly useful in veterinary fields such as horse breeding.

Advantageously, following the methods according to the invention, the neutrophil activation status is detected and/or measured via an immunological reaction wherein MPO is specifically (immuno)captured (only MPO is captured by a first antibody or at least the hypervariable portion thereof) preferably firstly via MPO-recognizing antibodies and then detected either directly via the enzymatic reaction of MPO or via a reaction with a specific labeled compound such as a chromogen, a fluorigen, or any other type of label, either directly (detection of MPO activity; MYELO-SIEFED) or indirectly ("immunological sandwich" with a second MPO antibody or at least a hypervariable portion thereof and possibly a further enzyme-bearing antibody that can recognize the second antibody, followed by the detection of this enzyme activity; MYELO-ELISA).

Said MPO-recognizing or MPO-specific first antibody can be a polyclonal or monoclonal antibody or its hypervariable portion or fragment thereof, an engineered antibody such as a humanized antibody (all obtainable by techniques well known in the art) as long as it is specific in their recognition of MPO in a complex medium possibly containing other types of peroxidases.

An aspect of the invention relates to the first monoclonal antibody or its hypervariable portion raised against equine MPO, which was not available hitherto.

The methods according to the invention, in particular the MYELO-ELISA and the MYELO-SIEFED, are particularly useful for the measurement of equine myeloperoxidase and find advantageous use in veterinary medicine, the methods being used in the diagnosis and/or the prediction of susceptibility to diseases correlated with neutrophil activation or inactivation, or being used to evaluate the immunological status of a horse. The SIEFED methods of the invention are also useful to study the effects of ligands (drugs) that interact with myeloperoxidase or to screen new compounds that interact with myeloperoxidase.

The methods according to the invention that make use of specific antibodies, are not restricted to the measurement of equine MPO originating from neutrophils. They can easily be extended to the measurement of MPO from mammals other than horses, including humans. It should be said that the first antibody (or its hypervariable portion) specifically recognizing equine MPO does not recognize that of other species (Serteyn et al., 2003, Ann. Med. Vet. 147:79-93). Species-specific antibodies can be raised using standard techniques if not already (commercially) available. The methods of the invention, in particular the described SIEFED method, are also not defined to MPO per se but can easily be extended to other enzymes, including but not limited to elastase, trypsin, . . . .

The biological sample or medium is preferably a biological fluid which can be obtained from said mammal, preferably a horse. Such biological fluid could be a cellular biological fluid or an acellular biological fluid. Said biological fluid could be venous and capillary blood serum or plasma, seminal fluid, broncho-alveolar fluid, pleural fluid, sputum, nasal fluid, ascites fluids, synovial fluid, gastric bowel and faecal derivate samples or cerebrospinal fluid.

The biological sample or medium could also be an extract obtained from various tissues of a mammal or other complex biological samples or media which may also comprise other molecules such as proteins (albumin, lipoprotein) and reducing agents that may interfere with adequate MPO measurement as observed for tests known in the art.

Therefore, contrary to methods of the state of the art as described for instance in WO 99/61907, the immunological detection with methods according to the invention allows to assess the natural defense capacity or ability of a mammal facing infection by measuring specifically the myeloperoxidase content originating from neutrophil cells and neutrophil cells only.

The methods according to the invention also apply to some specific diagnostic assays already proposed for the horse such as the detection of diseases of inflammatory origin, which may affect said mammal, especially the horse.

Below, some more detailed information is given on the MYELO-ELISA and the MYELO-SIEFED assays (kits or devices) that were developed (see FIGS. 1 and 2 for a general scheme). The acronym ELISA stands for Enzyme-Linked Immuno Sorbent Assay and the acronym SIEFED stands for Specific Immunological Extraction Followed by Enzymatic Detection.

The MYELO-ELISA immuno assay or method comprises the following steps. First myeloperoxidase from a biological sample taken from a mammal, preferably a horse, healthy or suspected to be diseased is immunocaptured. Immunocapture is by specific immobilized first antibodies (immobilized on a solid support such as a plastic surface of a multiwell plate). The capturing step is followed by the binding on the immobilized myeloperoxidase of another antibody (the second antibody) that is coupled to an enzymatic marker, used to reveal the reaction between the first antibodies and the myeloperoxidase. Said MPO-specific antibodies are obtained with a highly purified myeloperoxidase molecule that can be a natural or a recombinant myeloperoxidase. Preferably a recombinant myeloperoxidase is used.

The (MYELO-)SIEFED immuno assay (kits or devices) or method is a novel and inventive method that comprises the following steps. First there is the capture of an enzyme, for instance myeloperoxidase, obtained from a mammalian sample, preferably a horse sample. The sample may be taken from a healthy individual or one suspected to be diseased. The enzyme to measure and/or detect is captured by a first immobilized specific antibody (immobilized on an insoluble solid support such as a plastic surface). The (immuno)capturing of the enzyme, for instance MPO, is then followed by a washing step, whereby components that can interfere with the measurement are washed away. Enzymatic activity of said enzyme, for instance myeloperoxidase, fixed on its first specific antibody is then determined by specific techniques described hereafter. This technique does not require any extensive and laborious purification steps which would otherwise be required when working with complex samples.

Another aspect of the present invention concerns immunoassays kits (or kits-of-parts or devices) comprising the elements for performing at least the step of these two immunoassays (MYELO-ELISA and (MYELO-)SIEFED immunoassays). Such elements may include the MPO recognizing antibodies, possibly labeled and preferably fixed upon solid supports (such as multiwell plates (of any format) or beads), chromogens and other substrates, buffers, diluents or washing solutions, blocking agents.

In an embodiment according to the present invention, the kits (or devices) are kits-of-parts (possibly comprising different parts of the elements for performing the method steps).

Another aspect of the invention relates to neutrophil cell activation status devices comprising one of the above-described ELISA and/or SIEFED kits.

A particular embodiment of the invention concerns a sandwich ELISA kit or method whereby the second antibody is recognized by a "revelation" antibody labelled with an enzyme, such as an alkaline phosphatase allowing the detection of the immunological complex [the first immobilized MPO-recognizing antibody—MPO—the second MPO recognizing antibody]. By turning a substrate into a colored, phosphorescent or fluorescent reaction product, the enzyme that is linked to said second antibody allows the detection and/or quantification of the bound MPO molecule present in the sample. In a particular embodiment of the invention, the "revelation" antibody was labelled with an alkaline phosphatase and the substrate was N-nitrophenyl phosphate. Many other suitable labels and substrates are, however, known to the person skilled in the art.

Another embodiment of the invention is related to a MPO-SIEFED method, kit and device whereby the MPO present in the sample is captured by immobilized specific antibodies. In this particular case, its enzymatic activity was detected via a fluorimetric reaction product of a substrate such as Amplex® Red, (10-acetyl-3,7-dihydroxyphenoxazine, a "fluorogen") when said substrate is added to the bound MPO in the presence of $H_2O_2$. Many other detection techniques and means are available to the person skilled in the art.

It was surprisingly found that the detection sensitivity of the MPO-SIEFED method could be significantly increased by the addition of nitrites which significantly enhanced fluorescence. The preferred amount of nitrite ($NO_2^-$) to add to the reaction mixture is comprised between about 0.05 to about 0.7 mg/ml and preferably is about 0.2 mg/ml. Nitrite is preferably added under the form of a salt such as a Na-salt or any other alkali or earth alkali salt (such as Li, K, Rb, Cs, Be, Mg, Ca, Sr salts) except toxic salts (such as presumably Ba, Ra or Fr salts). Amplification of the detection signal makes it possible to accurately measure and detect the enzymatic activity of an enzyme, for instance that of MPO originating from neutrophils, in the most complex (biological) media, tissues or samples.

In a particular and preferred embodiment of the invention, the sensitivity of the enzymatic detection was increased at least 2-fold, preferably at least 5-fold, most preferably at least 10-fold or 20-fold by using nitrite as fluorescence enhancer.

This technique of fluorescence enhancement is equally well applicable to the detection of other peroxidase activities, and is applicable not only to the described SIEFED methods, kits and devices, but to any detection method or kit that may require the use of a peroxidase enzyme.

A particular aspect of the present invention relates to the use of nitrite to enhance enzymatic detection of peroxidases. Nitrite in particular was found to increase a 10-acetyl-3,7-dihydroxyphenoxazine-induced fluorescence signal.

The interest of the above described detection techniques (ELISA AND SIEFED methods, kits and devices) is that they allow to know separately, if wanted, the total MPO concentration (active and inactive enzyme forms; by MYELO-ELISA) and the concentration of the active form only (by MYELO-SIEFED) that has been released and/or is present in biological samples, which may be complex samples.

During uncontrolled inflammatory processes, a release of active myeloperoxidase in biological fluids (e.g. blood) could be injurious for surrounding cells or tissues. SIEFED bioassays (kits or devices) allow determination of the active part of the enzyme (potentially toxic) whereas ELISA bioassays (kits or devices) will give information on the total concentration of the enzyme. Both tests are thus complementary.

The potential applications of ELISA and SIEFED for (equine) myeloperoxidase in particular are:
- the evaluation of the intensity of neutrophil activation and systemic or local inflammatory reaction, in acute or chronic inflammation pathologies (sepsis, septic shock, pulmonary inflammation pathologies, intestinal pathologies, laminitis).
- the follow-up of the activation of neutrophils during therapy (study of the effects of drugs administrated to the patient, preferably a horse), taking samples of the same diseased individual or mammal (preferably a horse) at different time intervals whereby the neutrophil activation status can be followed in time.
- the early diagnostic or forecasting of some pathologies.
- the evaluation of the ability of neutrophils to destroy micro-organisms (evaluation on isolated neutrophils), a test to be applied in immunosuppression pathologies.
- the evaluation of the natural defense capacity or ability of an individual or group of individuals to fight against infections.
- the measurement of myeloperoxidase capture by other cells (in relation with their ability to fight against micro-organisms and/or to destroy them).
- The screening and the selection of compounds, possibly inducing with the MPO and possibly affecting the activity of this MPO.

Therefore, the kit or device according to the invention is preferably a high throughput screening kit or device which comprises elements for measuring, screening, selecting and possibly recovering active compounds. Such 'active compounds' are elements selected from the group consisting of chemically or biologically synthesized molecules (including antibodies), purified new natural molecules, microorganism plants or animal extracts or a mixture thereof. These compounds are preferably MPO inhibitors (reversible or irreversible inhibitors). The term 'an enzyme inhibitor' is a compound or agent that combines with an enzyme in such a manner as to prevent the normal substrate-enzyme combination and the catalytic reaction. Preferably said kit or device is based upon a method which comprises the steps of

- capturing active MPO (preferably via MPO specific antibody or a hypervariable portion thereof) bound to a solid support, preferably the solid support of the SIEFED kit or device according to the invention,
- possibly measuring MPO activity, preferably by the SIEFED method above described,
- adding one or more compounds to the active MPO (bound to the antibody or a hypervariable portion thereof),
- measuring MPO activity after addition of the compound(s) and preferably after a washing step of the unbound compound(s),
- possibly comparing MPO activity before or after addition of the compound(s), and
- possibly recovering the compound(s) that interact with MPO.

When examining the ability of cells other than neutrophils to fight against micro-organisms and/or to destroy them, the bioassays that have been described above are then applied to samples containing said other cell type. By comparing MPO levels obtained for said cells with neutrophil MPO levels of the healthy individuals, an estimate can be made of the capacity or ability of said cells to fight infections by micro-organisms.

The above detection techniques (methods, kits or devices) can further find advantageous use in the study of the efficiency of certain medicaments such as immunomodulators. MPO levels of neutrophils that have been in contact with for instance said immunomodulators are then compared with MPO levels of non-treated neutrophil cells, said MPO levels being an indication for the neutrophil activation status and/or their ability to fight and/or destroy micro-organisms.

The detection methods according to the invention are in particular useful in the prediction, the diagnosis, possibly in a very early stage, and/or the follow-up of one of the following pathologies or diseases: inflammatory diseases, digestive pathologies, strangulated intestinal pathologies, sepsis, septic shock, chronic and acute pulmonary pathologies (with invasion of the alveoli by neutrophils), ischemia-reperfusion pathologies, articular pathologies (with presence of neutrophils in the joints), colics, allergies, infections, cardiovascular diseases, . . . .

The SIEFED detection method, kit or device according to the invention are further particularly useful for the in vitro evaluation of the inhibitory capacity on myeloperoxidase activity of drugs (either natural products obtained from plant extracts or from animal origin, or newly synthesized molecules), allowing to distinguish between a neutralizing effect of said drugs on the products of myeloperoxidase activity (stoichiometric anti-oxidant activity) or a direct inhibitory activity on the enzyme function itself (anti-catalytic activity).

A last aspect is related to the compound interacting with MPO activity and recovered by the method according to the invention, preferably a therapeutical or prophylactic compound which could be used in the treatment of one or more symptoms or diseases above described.

In a more general way, by comparing MPO levels measured via ELISA (active and inactive MPO measured) and SIEFED techniques (only active MPO measured), the efficiency of purification techniques can be assayed.

SHORT DESCRIPTION OF THE FIGURES AND DRAWINGS

Figure 3:
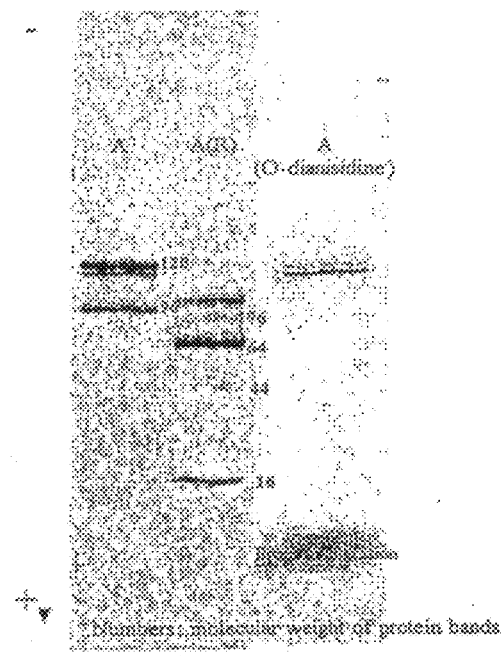

FIG. 3 represents the main steps of MPO purification: as visualised with electrophoresis of pure equine MPO in non-reducing conditions [A], in reducing [A(R)] conditions, and in non-reducing conditions with enzymatic activity detection on the gel [A(O-dianisidine)]. Purification steps comprised isolation of polymorphonuclear leucocytes (PMN) from blood, extraction of PMN, dialysis, chromatography (cationic exchange, gel filtration) and electrophoresis.

Figure 4:
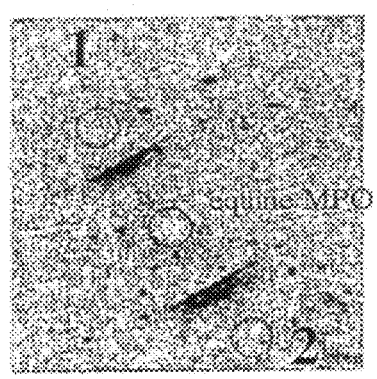

FIG. 4 represents the results of an immunodiffusion test for rabbit IgG (1) and guinea pig IgG (2) obtained against equine MPO. The antibodies used in this test were polyclonal antibodies (IgG) purified by affinity chromatography on Protein A Sepharose.

Figure 5:
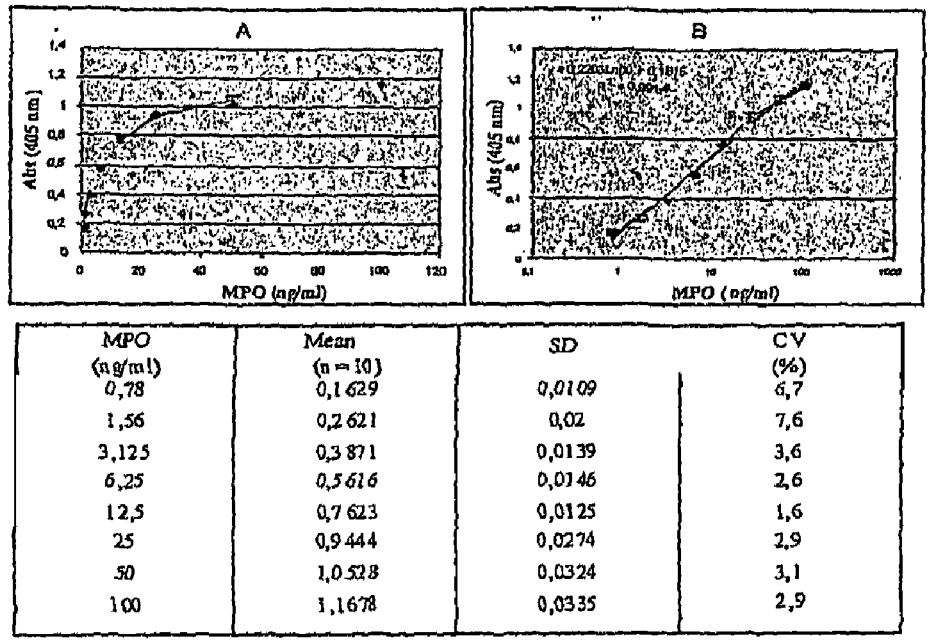

FIG. 5 represents MPO standard curves for a MYELO-ELISA performed with polyclonal antibodies: before (A) and after (B) logarithmic transformation (n=10). Mean OD values, standard deviations (SD) and coefficients of variation (CV) are given in the corresponding table.

Figure 6:
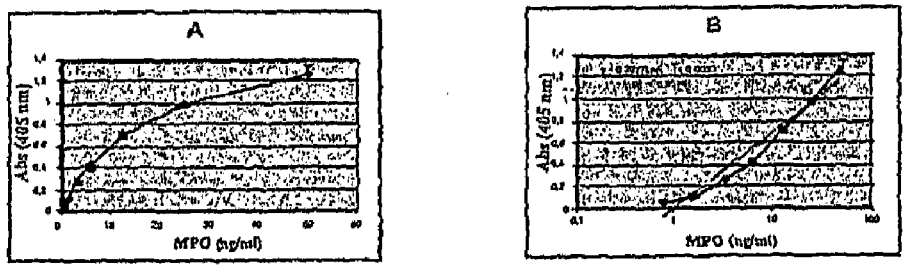

FIG. 6 represents MPO standard curves for a MYELO-ELISA performed with monoclonal antibodies: before (A) and after (B) logarithmic transformation (n=10). Mean OD values, standard deviations (SD) and coefficients of variation (CV) are given in the corresponding table. Curves were found to be linear for MPO concentrations ranging between 3.125 and 50 ng/ml.

Figure 7:
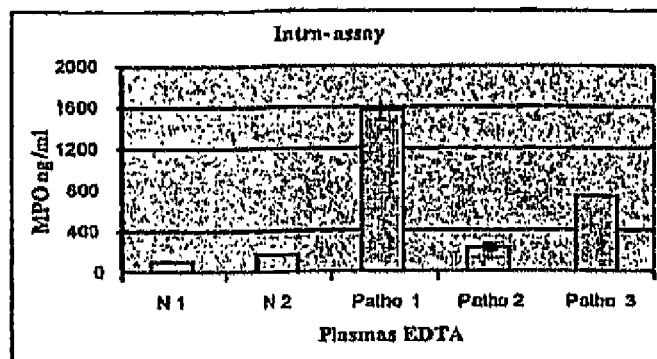

FIG. 7 represents an intra-assay variation for MYELO-ELISA assays performed with polyclonal antibodies. EDTA Plasmas taken from horses with (Patho) or without (N) pathologies were diluted 40 times. Mean OD values, standard deviations (SD) and coefficients of variation (CV) are given in the corresponding table.

Figure 8:
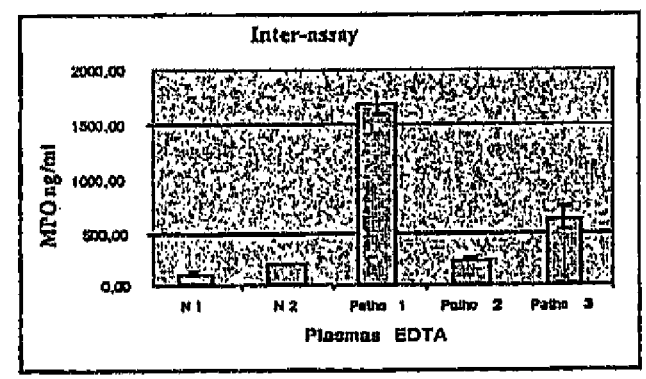

FIG. 8 represents an inter-assay variation for MYELO-ELISA assays performed with polyclonal antibodies. EDTA Plasmas taken from horses with (Patho) or without (N) pathologies were diluted 40 times. Mean OD values, standard deviations (SD) and coefficients of variation (CV) are given in the corresponding table.

Figure 9:
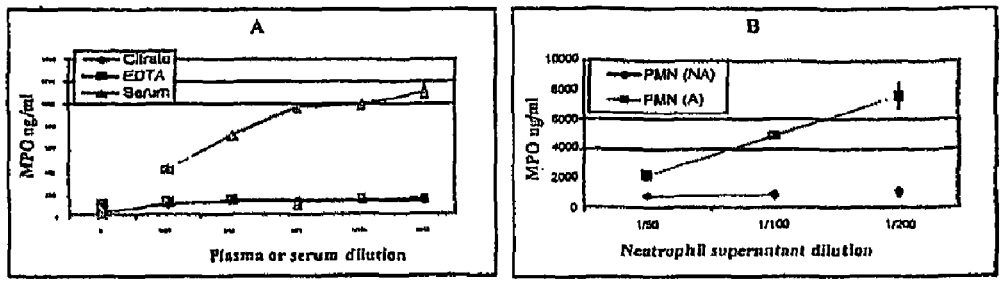

FIG. 9 represents the effects of sample dilution on MPO values measured via ELISA in serum and plasma (A), and on MPO values measured via ELISA in the supernatant of stimulated (PMN A) or non-stimulated (PMN NA) equine neutrophils (n=3).

Figure 10:
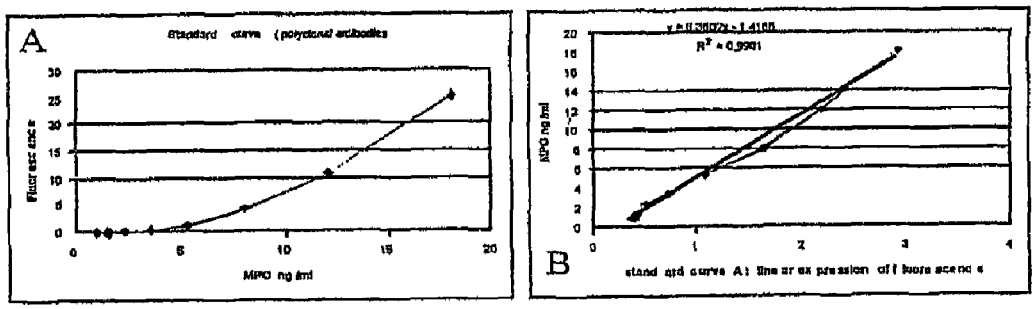

FIG. 10 represents the results of a MYELO-SIEFED performed with polyclonal antibodies: before (A) and after (B) linear transformation (n=3). Mean OD values, standard deviations (SD) and coefficients of variation (CV) are given in the corresponding table. Incubation time of MPO with immobilized antibodies: 2 h at 37° C. Enzymatic activity was detected with Amplex® Red as substrate.

Figure 11:
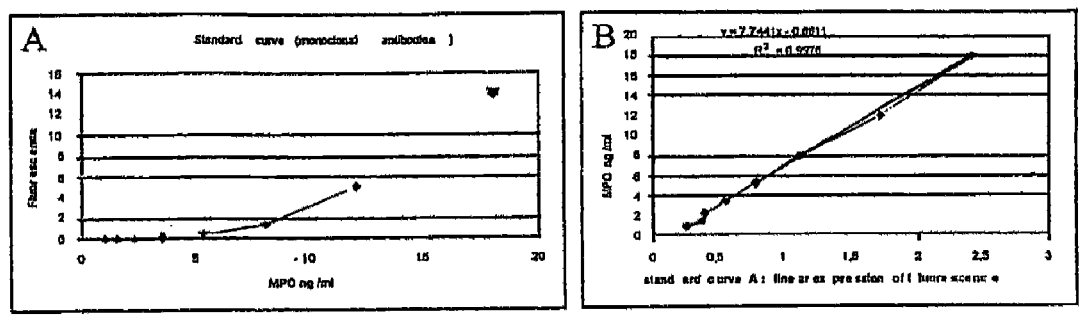

FIG. 11 represents a MPO standard curve for a MYELO-SIEFED performed with monoclonal antibodies: before (A) and after (B) linear transformation (n=3). Mean OD values, standard deviations (SD) and coefficients of variation (CV) are given in the corresponding table.

Figure 12:
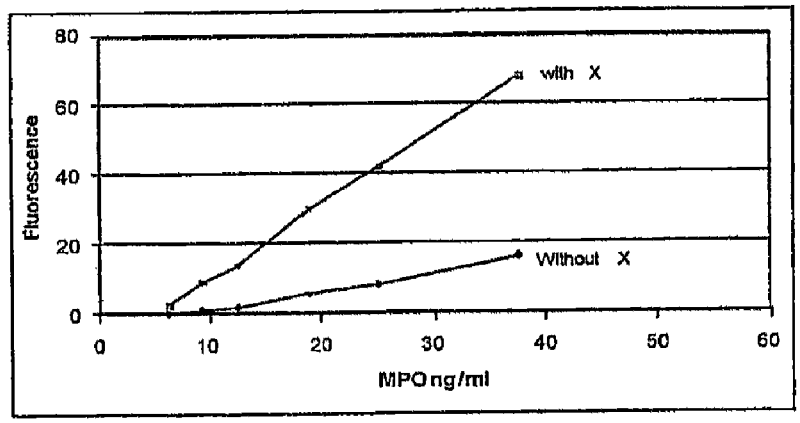

FIG. 12 represents a MPO standard curve for a MYELO-SIEFED and shows the positive effect of adding nitrites as enzymatic reaction enhancer when Amplex® Red is used as substrate (MYELO-SIEFED+).

Figures 13, 14:
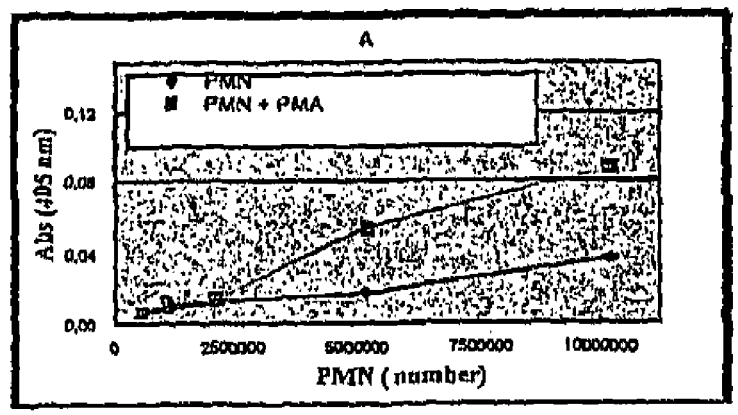

FIG. 13 demonstrates that a MYELO-SIEFED performed with polyclonal antibodies can be efficiently used for the detection and measurement of MPO enzymatic activity in biological samples. A distinction could be made between MPO levels of non-stimulated (PMN) neutrophils and of neutrophils that were stimulated by phorbol myristate acetate (PMN+PMA). Increasing numbers of PMN were used.

FIG. 14 demonstrates that a MYELO-SIEFED can be efficiently used to detect and measure MPO enzymatic activity in different biological samples such as plasma and seminal liquid, and that a distinction can be made between normal (healthy) and pathological samples. SD: standard deviation; CV: coefficient of variation; N: normal samples; P: pathological samples.

Figure 15:
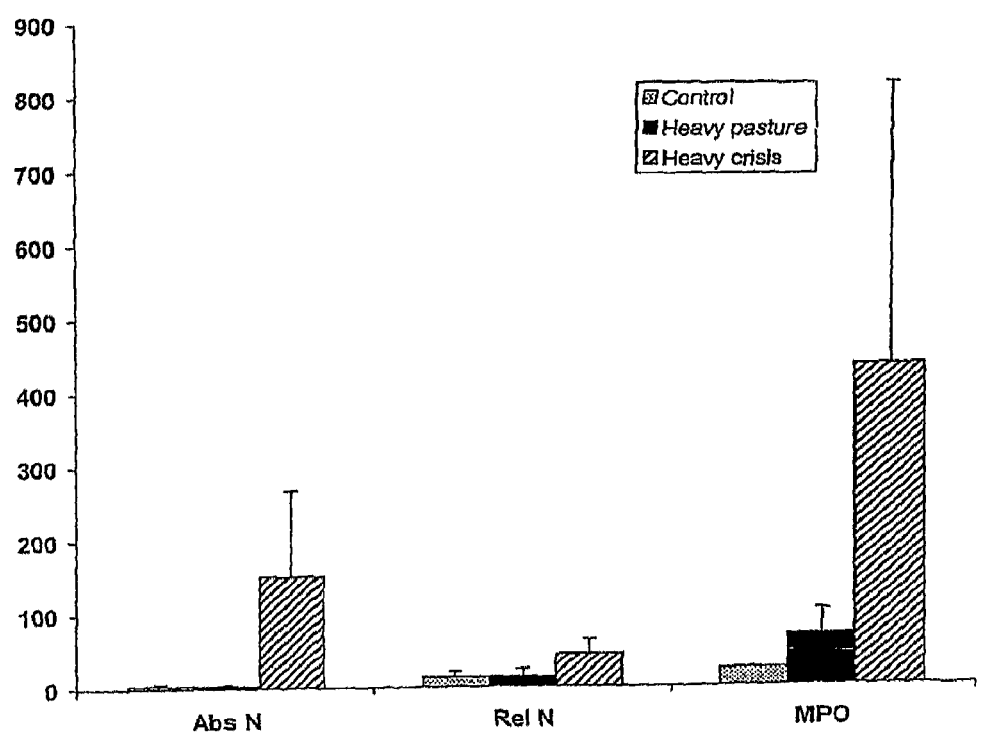

FIG. 15 represents absolute neutrophils counts (in number of cell $10^4$/ml) (Abs N); relative number of neutrophils (in %) (Rel N) and BAL MPO (ng/ml) (MPO) from 7 heavy horses either in crisis or after 2 months on pasture and in control health horses (significantly different from healthy horses and heavy horses in remission; +significantly different from healthy horses).

Figure 16:
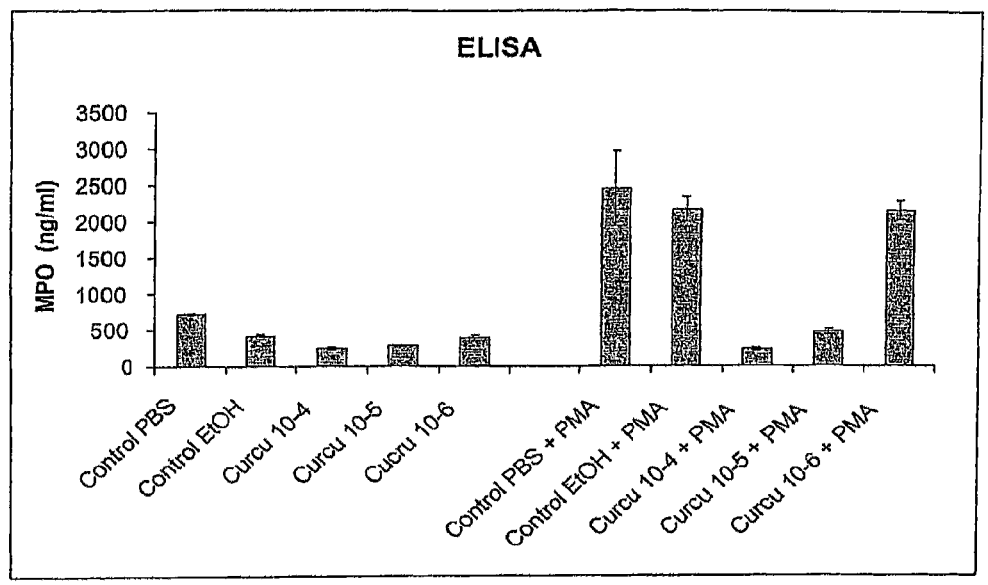

FIG. 16 represents the inhibitory effect of curcumin on MPO release by neutrophils incubated in PBS buffer with or without stimulation with phorbol myristate acetate (PMA) (Curcumin (Curcu) was dissolved in ethanol. MPO was measured by ELISA in the supernatant of activated neutrophils).

Figure 17:
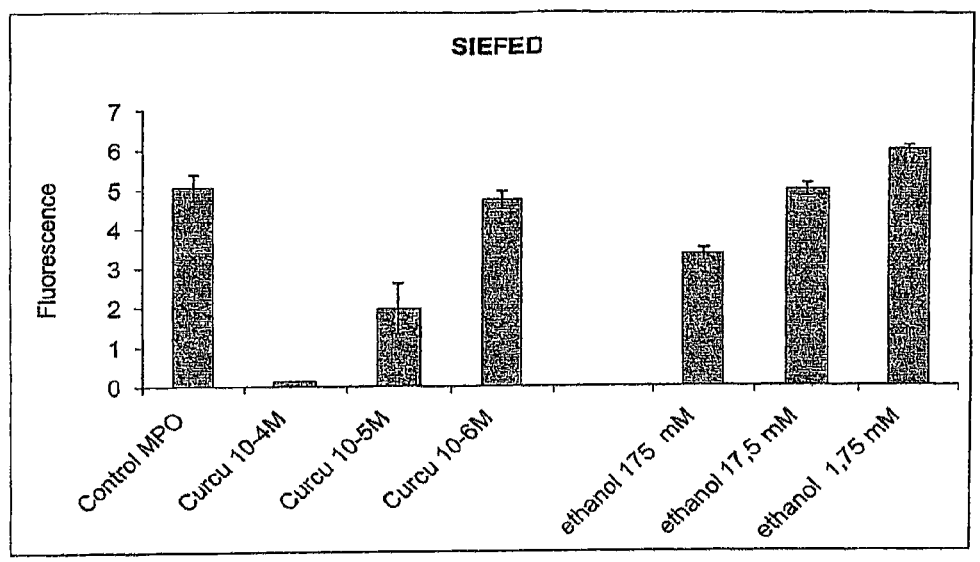

FIG. 17 represents the inhibitory effect of curcumin on MPO activity. Concentration of MPO used: 9 ng/ml. The incubation time of curcumin with MPO before assay by SIEFED was 30 min. (The most concentrated curcumin solution was prepared in ethanol (175 mM) and dilutions of this concentrated solution were performed with PBS buffer).

DETAILED DESCRIPTION OF THE INVENTION

The present invention will now be described in detail in the following description of preferred embodiments of the present invention in reference to the enclosed figures.

The examples given below are offered by way of illustration, not by way of limitation.

EXAMPLES

Example 1

Purification of Equine Myeloperoxidase (MPO)

MPO was extracted from equine polymorphonuclear leucocytes (PMN) isolated from whole blood by sedimentation on a Ficoll-Paque density gradient. The purification was performed, with some modifications, following a previously described technique (Mathy-Hartert et al. 1998, Can J Vet Res. 62:127-32). Briefly, packed neutrophils were homogenized in sodium acetate buffer (0.2 M Na acetate; 1 M NaCl; pH 4.7) containing 1% cetyltrimethylammonium bromide (CETAB). The supernatant was collected by centrifugation and dialysed. Dialysis allowed precipitation of elastase and cathepsin G, while MPO was recovered in the supernatant. MPO was further purified by two chromatographic steps: ion exchange (Hiload SP Sepharose) with a NaCl gradient followed by gel filtration chromatography on Hiload Superdex 200 (elution with a NaCl-acetate buffer). The purity of MPO was assessed by enzymatic assays (orthodianisine technique) and by electrophoresis on polyacrylamide gels (ExcelGel SDS, gradient 8-18) (FIG. 3).

Example 2

Preparation and Purification of MPO Antibodies

For the production of polyclonal antibodies, antisera were raised in rabbits and guinea pig by intradermic injection of 100 µg of pure equine MPO. Booster injections were given at 15 days intervals with 50 µg of MPO. Blood samples were collected 10 days after each booster injection. After the last booster, the two animals were ex-sanguinated. Purification of the polyclonal antibodies (immunoglobulin, or IgG) from antisera was realized by affinity chromatography on a Protein A Sepharose column. Reactivity of the two antibodies against equine MPO was tested qualitatively by immunodiffusion (Ouchterlony technique) (FIG. 4).

Monoclonal antibodies and corresponding hybridoma have been obtained and tested for their reactivity against equine MPO. Among several convenient hybridoma, two were selected for the production of monoclonal antibodies to be used in the ELISA and SIEFED techniques.

Example 3

Figure 1:
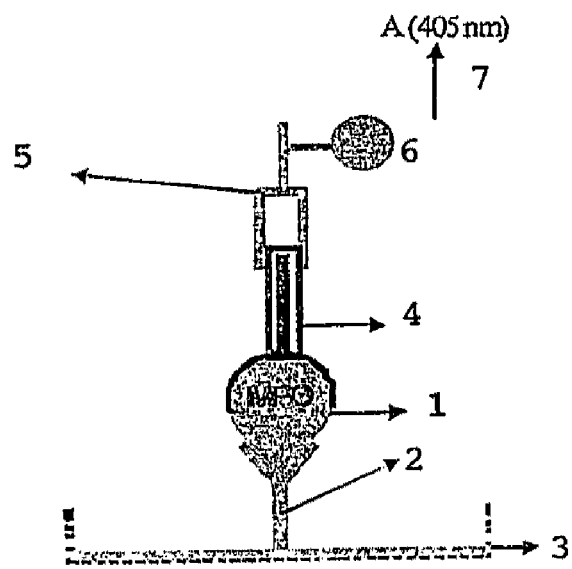
FIG. 1 represents a general scheme of a MYELO-ELISA.

Sandwich ELISA Technique to Measure Total (Active and Inactive) Neutrophil MPO Content For the measuring of the activation status of neutrophils by measuring both active and inactive MPO (1), a classical "Sandwich" Elisa method was designed (FIG. 1). The ELISA developed for MPO (1) measurement is further referred to as a MYELO-ELISA. Rabbit IgG, the primary antibody (2), is immobilized (coated) in excess (3 µg/ml) onto microtitration wells (3) (Cliniplate EB, Labsystem). Standard or test antigen (equine MPO (1)) is incubated overnight with the primary antibody (2) at 4° C. After washing (0.9% NaCl solution containing 0.1% tween 20), the immobilized antibody-antigen complex is incubated (2 h, 37° C.) with an excess (5 µg/ml) of guinea pig IgG, the secondary antibody (4). After washing, a third antibody (5) produced against guinea pig IgG is added. This third IgG (5) (goat IgG) is labelled with alkaline phosphatase (6) and recognizes the "sandwich" complex "primary antibody-MPO-secondary antibody". After washing, phosphatase activity is detected by incubation (30 min, 37° C., in the darkness) with a paranitrophenyl phosphate solution (phosphatase substrate, Sigma). The reaction is stopped with NaOH and the absorbance (405 nm) is measured with a Multiscan Ascent apparatus (Labsystem) (7). All the volumes added into the wells comprise 100 µl, except for washing (300 µl) and for the substrate solution (200 µl). Controls (blank) and dilutions of the standard MPO and samples were established with dilution buffer [PBS (20 mM phosphate, 137 mM NaCl and 2.7 mM KCl pH 7.4) to which 5 g/L bovine serum albumin and 0.1% tween 20 was added]. The same ELISA technique was developed also for monoclonal antibodies as primary antibody.

The absorbance response obtained with such ELISA assays is directly proportional to the quantity of sandwich complex formed, in other words to the concentration of MPO in the sample.

Example 4

SIEFED Technique to Measure Active Neutrophil MPO Content

Figure 2:
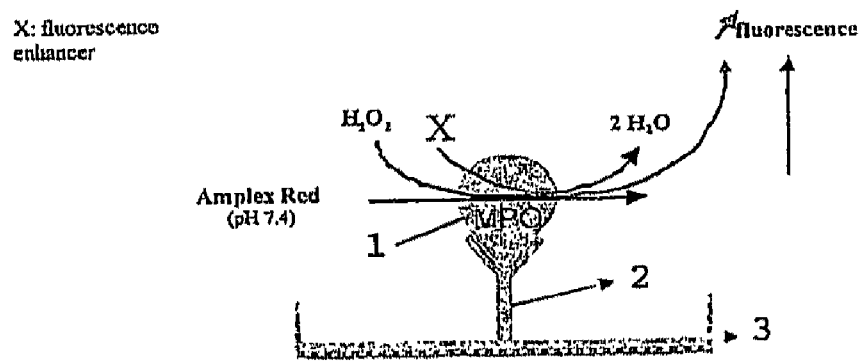
FIG. 2 represents a general scheme of a MYELO-SIEFED with fluorescence amplification or enhancement.

SIEFED ("specific immunological extraction followed by enzymatic detection") is an immunodetection technique consisting of two steps:

the capture of an enzyme such as (equine) MPO (1) from biological samples by immobilized specific antibodies (2), followed by the enzymatic detection of the enzyme such as MPO (1) immobilized on the antibodies that are coated onto a solid support (3)(FIG. 2).

Contrary to the above described ELISA test, the SIEFED techniques measures active MPO only. In a way, both tests are thus complementary.

As for the ELISA test, the primary antibody, that captures MPO, is rabbit IgG (3 µg/ml). Standard MPO or unknown sample is incubated 2 h at 37° C. After washing, the peroxidase activity of MPO is detected by adding 100 µl of a 10 µM $H_2O_2$ solution and 40 µM of Amplex® Red (10-acetyl-3,7-dihydroxyphenoxazine; Molecular Probes) in phosphate buffer (50 mM, pH 7.5). After incubation in the darkness (30 min, 37° C.), the fluorescence is read at 590 nm with a Fluoroskan Ascent apparatus (Labsystems). The volumes of the primary antibody and the sample put in the wells, are 200 µl. Controls (blank) and dilutions of the samples are established with dilution buffer.

The same technique was developed for monoclonal antibodies that recognize the active form of MPO.

An original technique of enhancement of the peroxidase response of MPO has been developed, leading to an increased fluorescence response and to an increase of the sensibility of the MYELO-SIEFED. Enhancement of fluorescence was surprisingly obtained when adding a defined concentration of nitrites ions (about 10 mM) to the Amplex® Red solution. This sensibility enhancement technique is applicable to the enzymatic detection of other peroxidases as well in other medical or industrial detection processes.

Results and Discussion

Purified MPO Retained its Enzymatic Activity

Electrophoresis of purified equine MPO shows 3 bands: two at molecular weight near 120 kDa (native enzyme) and one at 96 kDa (precursor) (FIG. 3). When MPO is treated with dithiothreitol (prior to loading onto the gel in order to break internal disulphide bridges and to release the subunits structure of the enzyme), the band at 96 kDa remains, the bands at 120 kDa disappear and two bands appear at 64 kDa and 16 kDa corresponding respectively to the heavy and light subunits of the enzyme. A weakly stained band also appears at a molecular weight of 40 kDa, that can result from an intramolecular disulphide bridge breaking or that represents the heavy subunit without the prosthetic group. Another weak band appears at 76 kDa, that could be attributed to the hemi-enzyme (heavy and light subunits). The peroxidase activity (defined as the stain of the protein bands on the gel by orthodianisidine in the presence of $H_2O_2$) showed activity at the 120 kDa bands under non reducing conditions.

Raised Polyclonal and Monoclonal Antibodies Efficiently Recognize MPO

A good reactivity (presence of precipitation arcs) was observed between equine MPO and IgG from rabbit and guinea pig (FIG. 4, Ouchterlony detection technique). Similar results are obtained with several monoclonal antibodies, two of which were selected for further ELISA and SIEFED development.

MPO Standard Curve for the Developed ELISA Test

An MPO standard curve was obtained by plotting the absorbance values at 405 nm as a function of standard MPO concentrations measured via the developed ELISA test. This standard curve is a classical one, reaching a plateau for the highest MPO concentrations. An almost linear curve is obtained when MPO concentrations are expressed in the logarithmic form (FIG. 5). The table shown in FIG. 5 lists the absorbance values (405 nm), standard deviation (SD) and intra-assay variation coefficient (CV in %) obtained for an equine MPO 2-fold dilution series ranging from 0.78 to 100 ng/ml MPO in the dilution buffer (for the composition: see Example 3).

Standard curves obtained with a monoclonal antibody are shown in FIG. 6. The results are similar to those obtained with the polyclonal antibodies (FIG. 5).

MPO standard curves allow quantification of the amount of MPO detected. Monitoring of disease progression benefits from such quantification. By comparing mean MPO levels of healthy with diseased individuals, cut-off values can be established that allow distinction between healthy and diseased mammals. Preferably such cut-off values are established for the different biological samples assayed for neutrophil MPO levels.

Developed MPO ELISA Test Allows Detection of Equine MPO in Acellular Complex Samples such as Plasma MPO levels were detected in biological samples consisting of plasma drawn from blood with different anticoagulants (EDTA, citrate, heparin), serum (FIG. 9A) or supernatant isolated from stimulated or unstimulated neutrophils (PMN) (FIG. 9B).

It was found that the best sampling technique for MPO measurement in plasma (as true witness of in vivo neutrophil degranulation) is to collect blood onto EDTA, which allows one to get a plasma value of MPO that is stable with time. The plasma drawn onto heparin and the serum allow in vitro degranulation of neutrophils, leading to artefactual values of MPO.

An important liberation of MPO was observed in the supernatant of excited neutrophils in comparison to non-excited ones. Intra- (FIG. 7) and inter- (FIG. 8) assay coefficients of variation (witness of the precision of the technique) were established for plasma taken from healthy horses and horses with inflammation pathologies.

The highest concentrations of MPO were observed in plasma from horses with intestinal strangulated pathologies.

The above demonstrates that the tests of the present invention are sensitive, accurate and clearly able to make a distinction between healthy and pathological animals. They further demonstrate that the measurement of plasma MPO can be taken as the witness of neutrophil activation and are positively correlated to certain pathologies.

The test was also applied with success to peritoneal fluids and seminal liquids.

Sensitivity and Precision of the Developed ELISA Test

For the developed ELISA test for equine MPO (MYELO-ELISA), the sensitivity of the assay is about 2 ng/ml. Good intra- and inter-assay precisions are obtained for standard curves (inferior to 8%) and biological samples (generally inferior to 10%). The mean MPO value measured in normal horses was 181.8±64.7 ng/ml in EDTA-anticoagulated plasma (n=38).

Myeloperoxidase Concentration in Bronchoalveolar Lavage from Healthy and Heavy Horses In horses, recurrent airway obstruction or heaves is known to induce intra-alveolar increase of neutrophils as observed in bronchoalveolar lavage fluids (BAL). Myeloperoxyidase (MPO) is a specific enzyme of neutrophil granules with a strong oxidative activity which most probably plays a role in the pulmonary inflammation observed in horses suffering from heaves. It has never been measured in horse's BAL.

Seven horses suffering from heaves were exposed to moldy hay until they reached a maximum change in pleural pressure ($\Delta$Pplmax)>15 $CmH_2O$. At that point, BAL were performed. The BAL cytology, i.e. total cell count and neutrophils percentages, was immediately performed, while MPO concentration in BAL supernatant (centrifugation 10 minutes at 1000 g) was immediately determined using a specific enzyme-linked immunosorbent assay (ELISA) with polyclonal antibodies raised against equine MPO (Patent nr 04447027.6). Tests were repeated on the same horses after they spent 2 months on pasture. Six healthy horses served as controls. Means were compared by an ANOVA and a probability of >0.05 was considered as significant. The relationship between absolute and relative neutrophils were assessed by linear regression on the gathered data.

Exposure to moldy induced significant increases in $\Delta$Pplmax (28.4±14.6 $CmH_2O$), in both absolute and relative neutrophils as well as in the MPO level (FIG. 1). After 2 months on pasture, the horses recovered a physiologic $\Delta$Pplmax (8.1±0.7 $CmH_2O$), while the absolute and relative number of neutrophils and the MPO concentration decreased significantly (FIG. 15).

There were no significant differences between neutrophils counts of control horses and heavy horses in remission, but their respective BAL MPO concentration were different, the MPO level from heavy horses being significantly higher. Correlation between MPO levels and neutrophils counts were significant, with R2 values of 0.671 and 0.825 for relative and absolute neutrophils respectively.

Effects of the Natural Polyphenols, Curcumin and Tetrahydrocurcumin (THC) on Activated Equine Neutrophils and on MPO Activity.

Neutrophils isolated from citrated blood of healthy horses were counted, suspended in phosphate buffer saline (PBS) at pH 7.4 and incubated 10 min at 37° C. with curcumin or THC at the final concentration of $10^{-4}$, $10^{-5}$ or $10^{-6}$ M. After incubation and centrifugation (1000×g, 10 min), the neutrophils were resuspended in PBS and either activated 30 min with $8\times10^{-7}$ M phorbol myristate acetate (PMA), with a simultaneous monitoring of the chemiluminescent response in presence of lucigenin ($5\times10^{-8}$ M), or activated in the same conditions followed by centrifugation and MPO measurement in the supernatant. MPO, marker of neutrophil degranulation, was measured by a specific ELISA assay raised against equine MPO. The effect of polyphenols on MPO activity was tested by SIEFED ("Specific Immunological Extraction Followed by Enzymatic Detection") method that allows the study of drug interaction with the enzyme without reaction medium interferences.

Curcumin and THC both had dose dependent inhibitory effects on the chemiluminescence response of and the MPO release by activated neutrophils, and on the MPO activity. The inhibition percentages were 70%, 44% and 60% for curcumin (10-5 M) and 12%, 18%, and 22% for THC (10-5 M) on chemiluminescence, MPO release and MPO activity respectively. The higher efficacy of curcumin can be explained at least partially by its chemical structure. The conjugated double bounds and the plane structure of curcumin seems to make easier the neutralisation of the radical species generated by activated neutrophils and the interaction of the drug with the active site of MPO. These inhibitory effects of curcumin on equine neutrophils and MPO activity arise therapeutic perspectives in equine pathologies with excessive inflammatory reactions.

SIEFED Technique to Measure Active MPO Levels in Tissue Extracts (MYELO-SIEFED) and to Distinguish the Active MPO Form from the Total MPO (Inactive and Active) Form in Biological Samples The enzymatic activity of MPO produces HOCl (hypochlorous acid) or NaOCl (sodium hypochlorite) and other oxidant species potentially toxic if the enzyme acts directly in contact with tissues or into the cells, thus in places other than in the phagolysosome. MPO can be present in biological fluids in an inactive form (inhibition by oxidation or by specific inhibitors). It is interesting to distinguish the active MPO from its inactive form in biological samples.

A direct enzymatic measurement of MPO in biological fluids is impossible by the presence of proteins, mainly albumin. Before measurement in complex biological medium, the enzyme would have to be extracted by long purification procedures implicating chromatography separation. The originality of the SIEFED technique lies in the fact that active MPO can be detected by performing two easy steps only, which are the capture of equine MPO from the biological sample by specific immobilized antibodies, followed, after washing (elimination of albumin and other proteins) by a direct detection of the enzymatic activity with an appropriate substrate (mainly high sensitivity).

Indirectly, the SIEFED technique will indicate any anomalies that might have arisen during MPO isolation and purification.

MPO Standard Curve for the SIEFED Test

A MPO standard curve was obtained by plotting the fluorescence values (corresponding to MPO activity), read at 590 nm, as a function of the standard MPO concentrations measured with the developed SIEFED test.

A standard curve obtained with increasing concentrations of MPO is shown in FIG. 10A. An almost linear curve is obtained with the mathematical transformation of the fluorescence values (FIG. 10B). The corresponding table of FIG. 10 lists the mean absorbance values, standard deviation, and intra-assay coefficient variation (CV (%)) as an indication of the assay precision) obtained for the measured MPO concentrations (2-fold dilution series). Reaction time with Amplex Red was 30 min. Incubation time of MPO with immobilized polyclonal antibody was 2 h at 37° C.

A similar standard curve was obtained when monoclonal antibodies were used (FIG. 11).

The addition of nitrite ions (about 10 mM) under the form of a salt (sodium salt) to the reaction medium could enhance until tenfold the sensibility of the SIEFED assay (FIG. 12).

Developed MYELO-SIEFED Test Allowed to Detect Active Equine MPO in Acellular Complex Samples such as Plasma MPO levels were measured via the developed SIEFED test in biological samples consisting of plasma, serum, seminal liquid (FIG. 12), and supernatant isolated from excited or not excited neutrophils (PMN) (FIG. 13).

MPO levels can be measured via SIEFED in biological samples, diluted or undiluted. Concentrated samples often have to be diluted to avoid interference of proteins (abundantly) present in the biological medium, especially albumin. The addition of an enhancer (nitrites) of the peroxidase enzymatic activity allows using a fivefold sample dilution.

Sensitivity and Precision of the Developed SIEFED Assay

The sensitivity of the SIEFED assay for active equine MPO, developed with polyclonal or monoclonal antibodies and addition of the nitrite enhancer was about 0.2 mg/ml. Good intra-assay precision was obtained for standard curves and for biological samples (inferior to 10

Study of the Effects of Two Natural Polyphenols on MPO Activity.

The SIEFED was applied to study the effects of two natural polyphenols (curcumin and resveratrol) on MPO activity. Incubation of the polyphenol with MPO, followed by MPO capture, washing and enzymatic detection, showed a direct dose dependent inhibitory effect of curcumin or resveratrol on MPO activity. These results (FIGS. 16 and 17) suggest a direct interaction between the drug and the enzyme or a modification of the enzyme structure by the drug.

| | Inhibitory percentages (%) on neutrophil activation by PMA or on in vitro MPO activity | | |
|---|---|---|---|
| | Drug Concentrations (M) | Curcumin | tetrahydrocurcumin |
| MPO assay by ELISA in the supernatant after neutrophils activation with PMA. | 10-6 | 0 | 17 |
| | 10-5 | 43.6 | 18 |
| | 10-4 | 83.5 | 41 |
| MPO activity (SIEFED) | 10-6 | 21.1 | 0 |
| | 10-5 | 60.4 | 22 |
| | 10-4 | 96.2 | 73.4 |

Table 1 represents the inhibitory effects of circumin and tetrahydrocurcumin on the myelperoxidase released by activated equine neutrophils. Total enzyme was measured by ELISA and active enzyme was measured by SIEFED (the measured inhibition results from a direct interaction between the enzyme and its inhibitor).

The invention claimed is:

1. A Specific Immunological Extraction Followed by Enzymatic Detection (SIEFED) method for measuring the activation status of neutrophil cells in a biological sample obtained from a mammal, the sample containing the neutrophil cells and/or enzyme released by the neutrophil cells, which method specifically measures the active enzyme content only, the content being correlated with the neutrophil cell activation status, the method comprising the steps of:
    immunocapturing the enzyme released by the neutrophil cells present in the biological sample by contacting the biological sample with a neutrophil enzyme specific polyclonal or monoclonal antibody immobilized on a solid support;
    washing to remove any components that can interfere with the measurement of the enzyme activity;
    adding a specific substrate that is transformed by neutrophil active enzyme into a detectable fluorometric reaction product that generates a fluorescence signal;
    adding an effective amount of nitrite to the reaction medium to enhance the generated fluorescent signal; and
    detecting and/or measuring the enzymatic activity of the immunocaptured neutrophil enzyme present which indicates the activation status of neutrophil cells in the biological sample.

2. The method according to claim 1, wherein $H_2O_2$ is added to the reaction medium.

3. The method of claim 2, wherein the substrate is 10-acetyl-3, 7-dihydroxyphenoxazine.

4. The method according to claim 1, wherein the biological sample is a cellular or acellular sample selected from the group consisting of arterial, venous and capillary blood, serum, plasma, seminal fluid, broncho-alveolar fluid, urine, saliva, endotracheal fluid, peritoneal fluid, uterine irrigation liquids, sputum, synovial fluid, nasal fluid, gastric bowel and faecal derivate samples, cerebrospinal fluid and tissue extracts.

5. The method according to claim 1, wherein the neutrophil cell activation status is measured and correlated to a disease and/or pathology.

6. The method of claim 1, which further comprises the steps of:
- comparing the active neutrophil enzyme values from subjects known to present an activation of neutrophils with normal neutrophil enzyme levels obtained from subjects without diseases; and
- relating the active neutrophil enzyme levels measured to a neutrophil cell activation status indicative of the presence or absence of inflammatory diseases or immunological diseases affecting the neutrophil activation status in mammals.

7. The method of claim 6, which further comprises comparing and correlating the quantified active enzyme level with a standard active enzyme curve.

8. The method of claim 1, wherein the mammal is a horse.

9. The method of claim 1, wherein the enzyme is myeloperoxidase.

10. The method of claim 1, wherein the enzyme is elastase.

11. The method of claim 1, further comprising the step of detecting and/or measuring the total active and inactive enzyme present in the biological sample by a second enzymatically labeled enzyme specific polyclonal or monoclonal antibody.

12. A Specific Immunological Extraction Followed by Enzymatic Detection (SIEFED) kit for measuring the activation status of neutrophil cells in a biological sample obtained from a mammal, which the kit specifically measures the active enzyme content only, the content being correlated with the cell activation status, the kit comprising:
- neutrophil enzyme-specific antibodies effective for immunocapturing the enzyme released by the neutrophil cells present in a biological sample obtained from a mammal, and
- a specific substrate effective for being transformed by immunocaptured active neutrophil enzyme into a detectable reaction product that generates a fluorescence signal which indicates the activation status of the neutrophil cells in the biological sample; and
- an effective amount of nitrite that enhances the generated fluorescent signal produced by the detectable reaction product.

13. The kit of claim 12, wherein the enzyme is myeloperoxidase.

14. The kit of claim 12, wherein the enzyme is elastase.

* * * * *

UNITED STATES PATENT AND TRADEMARK OFFICE
CERTIFICATE OF CORRECTION

PATENT NO. : 8,399,208 B2  Page 1 of 1
APPLICATION NO. : 10/597636
DATED : March 19, 2013
INVENTOR(S) : Serteyn et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1484 days.

Signed and Sealed this
First Day of September, 2015

Michelle K. Lee
*Director of the United States Patent and Trademark Office*